United States Patent [19]

Royston al.

[11] 4,451,570

[45] May 29, 1984

[54] IMMUNOGLOBULIN-SECRETING HUMAN HYBRIDOMAS FROM A CULTURED HUMAN LYMPHOBLASTOID CELL LINE

[75] Inventors: Ivor Royston, La Jolla; Harold Handley, Cardiff; J. Edwin Seegmiller, La Jolla; Linda F. Thompson, San Diego, all of Calif.

[73] Assignee: The Regents of the University of California, Berkeley, Calif.

[21] Appl. No.: 247,652

[22] Filed: Mar. 26, 1981

[51] Int. Cl.$^3$ .................. C12N 5/00; C12N 15/00; C12N 5/02; C12R 1/91

[52] U.S. Cl. .................................. 435/240; 435/241; 435/948

[58] Field of Search ............... 435/240, 241, 243, 244, 435/85, 86, 87

[56] References Cited

U.S. PATENT DOCUMENTS 4,172,124 10/1979 Koprowski et al. ................ 424/85

OTHER PUBLICATIONS

Croce et al., "The Use of Mouse-Human and Human-Human Hybridomas in Human Genetics and Immunology" *Somatic Cell Genetics*, Plenum Press (1982), pp. 55-68.

Croce et al., "Production of Human Hybridomas Secretina Antibodies to Measles Virus" *Nature* 288 (Dec. 4, 1980), pp. 488-489.

Levy et al., "Further Characterization of the W1-L1 and W1-L2 Lymphoblastoid Lines" *Journal of the National Cancer Institute*, 46 (1971), pp. 647-654.

Olsson et al., "Human-Human Hybridomas Producing Monoclonal Antibodies of Predefined Antigenic Specificity" *Proceedings of the National Academy of Sciences U.S.A.*, 77 (9-1980), 5429-5431.

Nowinski et al., "Human Monoclonal Antibody Against Forssman Antigen" *Science* 210, (10/1980), pp. 537-539.

*Primary Examiner*—Thomas G. Wiseman
*Assistant Examiner*—John Edward Tarcza
*Attorney, Agent, or Firm*—Bertram I. Rowland

[57] ABSTRACT

Novel human lymphoblastoid cells and hybridomas derived therefrom are provided. The cells are a HGPRT negative human B-cell line. The cells are readily fusible with lymphoid cells to produce hybridomas which secrete human monoclonal antibodies.

2 Claims, No Drawings

IMMUNOGLOBULIN-SECRETING HUMAN HYBRIDOMAS FROM A CULTURED HUMAN LYMPHOBLASTOID CELL LINE

The invention described herein was made in the course, or under, grants from the National Institute of Health.

BACKGROUND OF THE INVENTION

1. Field of the Invention

Since the seminal discovery by Kohler and Milstein ((1975) Nature 256, 495–497) for producing specific predefined antibodies by somatic cell hybridization, technology has been extensively applied for the preparation of murine monoclonal antibodies to a variety of haptenic and antigenic determinants. While the murine monoclonal antibodies can be used for diagnostic purposes, the antibodies are immunogens to humans and thereby their use is limited or excluded for therapeutic purposes.

2. Description of the Prior Art

Olsson and Kaplan, Proc. Nat'l. Acad. Sci. USA 77, 5429–5431 (1980) describe the establishment of a continuous culture of purely allogenic human hybridomas secreting specific human antibody having myeloma cells as the fusion partner. Nowinski et al., Science 210, 537–539 (1980) describe the isolation of a mouse-human hybridoma secreting a human monoclonal antibody against Forssman antigen. Croce et al., Nature 288, 488–489 (1980) describe the production of human antibodies from a hybridoma using as a fusion partner a HPRT-deficient human B-cell line. The hybridomas produced with peripheral lymphocytes secreted human IgM specific for measles virus nucleocapsids.

SUMMARY OF THE INVENTION

A human lymphoblastoid cell line is used for the production of hybridomas which secrete human monoclonal antibodies. The monoclonal antibodies find wide use in diagnostics as well as for therapeutic purpose.

DESCRIPTION OF THE SPECIFIC EMBODIMENT

A human lympoblastoid B-cell line is provided which is useful for generating immunoglobulin secreting human-human hybridomas. The subject cell line is characterized by being derived from the human lymphoblastoid B-cell line (B-LCL) designated as WI-L2, the subject cell line being referred to as UC 729-6 and having the A.T.C.C. designation No. CRL 8061 having been deposited on Mar. 25, 1981.

The subject cell line is an Epstein-Barr virus transformed cell, is hypoxanthine phosphoribosyl transferase (HPRT)-deficient (6-thioguanine resistant), and expresses IgM, with kappa light chains on both the surface and in the cytoplasm. Supernatants from the cell line are negative for IgA, IgG and IgM.

The subject cell line is efficient as a fusion partner. The subject cell line may be fused with immunized lymphoid cells to produce hybridomas capable of secreting monoclonal antibodies. The antibodies may be produced to a wide variety of haptens and antigens and may find use in immunoassays, as antigens for antibody production, passive immunization, treatment against infection, diagnosis and treatment of cancer, neutralizing virus infections and toxins, neutralizing drug overdoses, and the like. In addition to the production of IgM, the human-human hybridomas prepared with the subject cell line as a fusion partner offer opportunities for the production of complete human monoclonal IgA, IgG, IgE, and IgD.

The subject cell line was chosen to provide a stable cell line which is HAT medium sensitive and unable to metabolize hypoxanthine. The subject cell line is a subclone of the parent WI-L2 cell line, a human B-LCL cell line described in Levy et al., Cancer 22, 517–524 (1968); Levy et al., J. Natl. Cancer Inst. 46, 647–654 (1971). The parent cell line was obtained as a spontaneous line from the culture of the spleen of a boy with hereditary spherocytosis. Subsequent studies have shown evidence of the presence of Epstein-Barr virus. WI-L2 was treated with 25 micromolar 6-thioguanine and 6-thioguanine resistant clones isolated. UC 729-6 was selected as having a significant number of cells containing intracytoplasmic immunoglobulin, and then shown to be an efficient fusion partner.

For production of monoclonal antibodies, the subject cell line is fused with human cells from lymphatic tissue immunized against a haptenic or antigenic determinant. Various sources of lymphatic tissue may be employed. Spleen cells, lymph node cells, tonsils, and peripheral blood lymphocytes can be used, which have been previously immunized in vivo or in vitro. The host is immunized at least once, usually at least about two weeks prior to the removal of the lymphoid tissue for cell fusion. After freeing a single cell suspension of the lymphoid tissue of red blood cells and granulocytes, the viable mononuclear cells are suspended in an appropriate nutrient medium and non-adherent cells separated from the adherent cells. The resultant non-adherent lymphoid cell culture may then be fused with the subject cell line.

For in vitro immunization, a single cell suspension of cells from lymphatic tissue is prepared, viable cells isolated and seeded in nutrient medium, which includes the immunogen at a predetermined concentration. After sufficient time for immunization to occur, the viable cells are isolated and used for fusion. As above, lymphoid cells can be used from spleen, lymph nodes, tonsils, and blood. To immunize the lymphocytes, the lymphocytes are combined in an appropriate nutrient medium containing macrophages and immunogen to prime the lymphocytes. After sufficient time for priming, usually two to six days, the viable cells are isolated and employed for fusion.

Isolation of lymphocyte cells can be achieved with Ficoll-Hypaque gradient centrifugation and the viable cells grown in nutrient medium, containing about 10% FCS, about 40 µg/ml antigen and about $10^5$ macrophages/ml and the cells incubated for about three days to prime the cells and produce blast cells. The viable cells may then be used for fusion.

Fusion can be readily achieved in accordance with known techniques. Desirably, the Kohler and Milstein technique, as modified by Gefter et al., Somat. Cell Genet., 3, 231–236(1977) is employed. The method employs a relatively high concentration of polyethylene glycol with an excess of, usually at least a 2 to 1 ratio of lymphoid cells to the subject cell fusion partner. The time for the fusion is generally under about 3 minutes and the resulting cells rapidly washed of the non-ionic detergent. The subject cell concentration will generally be about $10^6$ to $10^9$ cells/ml with the lymphoid cell concentration being from about 2 to 3 times its fusion partner.

The cells are then seeded at relatively high concentrations in microplates on human foreskin feeder layers and grown in an appropriate nutrient medium containing standard HAT components. Littlefield, Science 145, 709–710 (1964). After culturing for a sufficient time, usually in excess of about 4 weeks, the hybridomas appear, with the absence of growth of the parent cells.

The supernatants of the resulting hybridomas are then monitored for human immunoglobulin production. Conveniently, antibodies to the heavy or light chain type can be used for assaying for the presence of immunoglobulin. Radioimmunoassays, nephelometric techniques, and the like may be employed.

Once positive wells are detected, the cells in the positive wells may be cloned under limiting dilution conditions. The resulting clones have been expanded and the monoclonal antibodies harvested in accordance with known procedures. The monoclonal antibodies may be freed of other proteins in accordance with known techniques, such as electrophoresis, chromatography, or the like.

Monoclonal Antibodies

In referring to monoclonal antibodies, it is intended to include not only IgM, but also IgG, IgE and IgA, IgD. Antibodies may be produced against any haptenic or antigenic compound of which there is an ever increasing number which have been involved in immunization. Illustrative compounds of interest, but clearly not exhaustive, are drugs, both naturally occurring and synthetic, such as opioids, amphetamines, barbiturates, steroids, catecholamines, dilantin, theophylline, histamine, PCP, cannabinoids, valproate, digoxin, and the like. Antigens of interest include a wide variety of hormones and other physiologically active proteins, histocompatibility antigens, cancer antigens, pathogen surface antigens, viral antigens, toxins, allergens, and the like.

For a more complete list of ligands of interest for use in diagnostics, see U.S. Pat. No. 4,193,983, particularly Col. 7–11, inclusive, which disclosure is incorporated herein by reference.

The monoclonal antibodies of the subject invention are homogeneous in the sense that the variable regions for the antibodies are constant. That is, better than about 90% of the antibodies are the same composition in the variable region, usually better than 95%. Normally, the immunoglobulin will have less than about 1 mole % of antibodies having chains of a different type from the dominant component.

By having a uniform composition of immunoglobulins, many advantages ensue. First, one is ensured of freedom from immunoglobulins specific for other than the predefined antigen. The presence of undesired immunoglobulins is disadvantageous for analytical work as well as for therapeutic purposes. Secondly, one is assured of a single binding site, as compared to antibody compositions obtained from serum. Third, one can obtain an exact titer for a specific determinant site, rather than averaging over the entire composition. With analytes, better control of cross-reactivities can be achieved with a homogeneous composition.

The subject human monoclonal antibodies can find use as antigens, either for the entire molecule or for the individual, L, H and J chains, or portions thereof, such as the variable and hypervariable regions. The antibodies may also be used as standards for assaying for the various types of immunoglobulins. The immunoglobulins, because of their homogeneity, can be used for sequencing to provide the genetic sequence for preparation of probes e.g. radioactively labeled DNA, isolation of the genes from the genome, or synthesis of genes or a portion thereof.

The subject human monoclonal antibodies find use in conventional applications for antibodies, such as immunoassays, cell sorting, electrophoretic analysis, histology, cytology and the like. Besides the conventional uses, the subject monoclonal human antibodies have additional therapeutic uses since they are allogeneic (another member of the same species) proteins and should not be immunogenic to a human host.

Because the human monoclonal antibodies should be acceptable to the human immune system, the monoclonal human antibodies can be used for induction of passive immunity. Among conventional immune sera which are presently available are antisera (non-monoclonal) for tetanus, hepatitis, vaccinia, mumps, rabies, pertussis, botulism, gas gangrene, varicella, Rh factor, as well as other diseases. These could very well be replaced by human monoclonal antibodies produced by this procedure.

The antisera are normally administered parenterally or by ingestion in dosages varying from 100 to 20,000 units, or in amounts based on immune serum of 0.005 to 1 ml/kg of the host. (Medical Pharmacology 6th ed. Edited by Meyers, Jaivetz and Goldfien, Lange Medical Publications, 1978, pages 612–615.) Particular dosages will vary depending upon the manner of administration. Various carriers or media can be used, such as physiological saline, capsules, plasma, or the like. Other additives may also be included, such as stabilizers, drugs, proteins, and the like.

The human monoclonal antibodies can also be used for site directed therapy. By preparing antibodies recognizing determinant sites of an organ, abnormal cell e.g. tumor, or infectious cell, the antibody can serve to direct a drug or other therapeutic means to such site and maintain such drug or therapeutic means at such site. For example, the antibodies can be attached to slow release particles containing a particular drug for treatment of an infection. The antibodies would bind to the infected site, maintaining a high localized concentration of the drug in the infected area.

Other uses include diagnosis, where the antibodies would be labeled with a radioisotope or fluorochrome reagent, providing for localization of the radioactive, or fluorochrome label at a particular site, and permitting radiography at a particular organ or other internal site.

The hybridomas can also serve as a concentrated source of messenger RNA or as a source of the genes for the light and heavy chains of immunoglobulins e.g. IgM and IgG.

The following examples are offered by way of illustration and not by way of limitation.

EXPERIMENTAL

A HAT-medium sensitive mutant cell line was obtained by subjecting the known human lymphoblastoid B-cell line WI-L2 25 micromolar 6-thioguanine and isolating mutants resistant to 6-thioguanine. A thioguanine-resistant clone was isolated and designated UC 729-6. The UC 729-6 cells are routinely grown in RPMI 1640 media supplemented with 10% FCS, 2 mM glutamine and $10^{-4}$M 6-thioguanine. UC 729-6 doubles in concentration every 17 hours. Feeder layer human foreskin fibroblasts (350Q) were supplied by Dr. D. Richman. CLL (chronic lymphocytic leukemia) cells which were employed had a cell surface phenotype of being T101+ (a monoclonal pan-T cell reagent) Royston et al. J. Immunol. 125, 725-731 (1980)) and were surface IgM λ+. The CLL cells did not secrete IgM containing the λ light chain and could not grow in continuous culture. The CLL cells were purified on a standard Ficoll-Hypaque gradient. The patient's white count was 2.13 times $10^5$ cells per $mm^3$ with 100% lymphocytes at the time the sample was drawn.

Cells were fused by the method of Kohler and Milstein, supra, as modified by Gefter et al., supra, in 40% polyethylene glycol and a ratio 2.5 CLL/1 UC 729-6. Cells were plated at a concentration of $5 \times 10^5$/ml on human foreskin feeder layer (350Q) in a 24 well plate (Costar) and grown in RPMI 1640 supplemented with 10% FCS, glutamine and standard HAT components. Hybridomas appeared after 5 weeks culture, while UC 729-6 control cultures failed to grown. As a result of the fusion, 12 hybridomas were established and four were studied, each secreting human immunoglobulin containing IgM with predominantly λ light chains along with traces of κ light chain. The hybridomas were designated 8A1, 8B1, 8C1, and 8C6.

The supernatants of the resulting hybridomas and the parental UC 729-6 were then subjected to a wide variety of tests for evaluation.

Nephelometric studies were performed with a Hyland laser nephelometer as described by Virella et al., J. Immunol. Forsch. 155, 279 (1979). Light scatter of a monochromatic laser beam due to antigen-antibody complexes was studied. Heavy chain type and concentration of antibody present in 25 μl, 50 μl and 100 μl of unknown supernatants (obtained from CLL X UC 729-6 hybridomas) were determined with nephelometric grade goat anti-human heavy chain (α, γ, μ) in comparison to known standards.

Hybridoma supernatants were concentrated 80-fold (Amicon) and incubated for 18 hours in immunodiffusion plates (Kallestad) containing goat antisera to human IgA, IgG, or IgM.

Hybridomas supernatants were electrophoresed for 1 hour on an agarose film (Corning) and allowed to diffuse overnight toward goat-anti human heavy chains (α, γ, μ) and light chains (κ, λ) in a humidified chamber at 23° C. The films were pressed, dried and stained with Coomassie Brilliant Blue, then destained and allowed to dry. Axelsen et al., Scand. J. of Immunology, 2, 1 (1973).

Surface light chains were detected on whole live cells using direct immunofluorescence by a simultaneous two-color technique with fluorescein conjugated rabbit anti-κ and rhodamine conjugated goat anti-λ. (Royston et al., J. Immunol., 125, 725-731 (1980)). Intracytoplasmic light chains were analyzed using the same reagents as described above with acetone fixed cells on slides. T101, which recognizes a 65kdalton antigen was used in an indirect assay with fluorescein conjugated rabbit F(ab')₂ anti-mouse IgG (Fc specific). A myeloma protein, RPC-5, of identical isotype to T101 ($IgG_{2a}$) was used as the negative control antibody.

Karyotyping for the hybridomas and the parental UC 729-6 was achieved by incubating the cells for 3.5 hrs in 10 mg/ml colcemed (Sigma) in PBS at 37° C. The cells were then incubated in 0.075M KCl for 30 min, washed and fixed in 3:1 methanol-glacial acetic acid. Slides were prepared and chromosomes identified for analysis.

The general characteristics of the parental line UC 729-6 and the hybridomas are shown in the following table, the data for the hybridomas being based on 4 different clones.

TABLE I

| | Cellular Characteristics* | |
|---|---|---|
| | Cell Type | |
| Characteristic° | UC729-6 | Hybridoma |
| sIg | IgMκ | IgMκ |
| cyIg | IgMκ | IgMκ and IGMλ |
| T65Ag | 0 | 99% |
| Marker Chromosome | 21p+ | 21p+ |
| Supernatant | | |
| IgM | none detectable[1] | 3-9 μg/ml |
| IgG | none detectable[2] | none detectable[2] |
| IgA | none detectable[2] | none detectable[2] |
| κ | none detectable[2] | trace |
| λ | none detectable[2] | Positive |
| Karyotype | diploid | tetraploid |

*Distinguishing characteristics between the parental UC 729-6 and hybrids 8A1, 8B1, 8C1 and 8C6.
°s - surface
cy - cytoplasmic
T65Ag - 65kdalton antigen present on human T cells and CLL cells.
[1]Lower limit of detection is .8μg/ml.
[2]Lower limit of detection is .5μg/ml.

The above table demonstrates that the hybridomas are capable of producing substantial amounts of immunoglobulin, in this case IgM. Immunoelectrophoresis of hybrid supernatants detected the presence of predominantly λ light chain with traces of κ light chain IgM. CLL supernatant from a 24 hr culture of fresh cells contained IgM. IgM secretion by the hybrids was confirmed by immunodiffusion of 80 X supernatant with a goat anti-human IgM gel plate (Kallestad). Supernatants of UC 729-6 were negative for IgM.

The light chain type analysis of the immunoglobulin present at the surface of the parental and hybridoma cells as well as in the cytoplasm is set forth in the following table.

TABLE II

| Expression of surface and intracytoplasmic Ig by UC 729-6 and hybridoma cells | | |
|---|---|---|
| | Stained with | |
| | Fluorescein labelled anti-Hu κ % | Rhodamine labelled anti-Hu λ % |
| Cell Surface Stain of | | |
| 729-6 | 12 (6/50) | n.d.* |
| 8A1 | 12 (5/40) | n.d. |
| 8B1 | 17 (7/40) | n.d. |
| 8C1 | 15 (6/40) | n.d. |
| 8C6 | 10 (4/40) | n.d. |
| Cell Cytoplasm Stain of | | |
| 729-6 | 12 (6/50) | n.d. |
| 8A1 | 30 (15/50) | 48 (24/50) |
| 8B1 | 28 (14/50) | 32 (16/50) |
| 8C1 | 38 (21/55) | 30 (15/50) |
| 8C6 | 30 (12/40) | 30 (15/50) |

*n.d. - not detectable

It is evident from the above results that a human lymphoblastoid B-cell can be a fusion partner for production of secretory hybridomas. Depending upon the particular lymphoid cell employed for the fusion, one can enhance the probability of obtaining the varying kinds of immunoglobulin specific for the desired determinant site. The subject invention shows high yields of immunoglobulins, which can be used in themselves as antigens, sources of their component parts, sources of the variable and hypervariable regions, as well as in diagnostics and therapy.

A further advantage in using the subject cells is that the virus used for the transformation, namely Epstein-Barr virus, is of well documented etiology and any contamination of the monoclonal antibody composition by the virus or a portion thereof is more readily detectable.

Although the foregoing invention has been described in some detail by way of illustration and example for purposes of clarity of understanding, it will be obvious that certain changes and modifications may be practiced within the scope of the appended claims.

What is claimed is:

1. A HAT sensitive human lymphoblastoid B-cell line UC 729-6, ATCC-CR1 8061.
2. A hybridoma cell line derived from the fusion of lymphoblastoid B-cell line UC 729-6 ATCC CRL 8061 fused with a lymphoid cell line.

* * * * *